(12) United States Patent
Yunoki et al.

(10) Patent No.: US 7,045,657 B2
(45) Date of Patent: May 16, 2006

(54) CATALYTIC GAS PHASE OXIDATION PROCESS

(75) Inventors: Hiromi Yunoki, Himeji (JP); Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 518 days.

(21) Appl. No.: 10/387,244

(22) Filed: Mar. 12, 2003

(65) Prior Publication Data

US 2003/0191343 A1 Oct. 9, 2003

(30) Foreign Application Priority Data

Apr. 3, 2002 (JP) .............................. 2002-101773

(51) Int. Cl.
*C07C 51/235* (2006.01)
*C07C 51/16* (2006.01)

(52) U.S. Cl. ...................... 562/532; 562/537; 562/538; 562/545

(58) Field of Classification Search ..................... None
See application file for complete search history.

(56) References Cited

U.S. PATENT DOCUMENTS

| | | | |
|---|---|---|---|
| 3,801,634 A | | 4/1974 | Krabetz et al. |
| 4,511,671 A | * | 4/1985 | Saito et al. .................. 502/242 |
| 4,837,360 A | | 6/1989 | Kadowaki et al. |
| 5,198,581 A | | 3/1993 | Kawajiri et al. |
| 5,206,431 A | | 4/1993 | Hashiba et al. |
| 5,276,178 A | | 1/1994 | Onodera et al. |
| 5,719,318 A | | 2/1998 | Kawajiri et al. |
| 6,028,220 A | | 2/2000 | Wada et al. |
| 6,399,818 B1 | * | 6/2002 | Tanimoto et al. ........... 562/546 |

FOREIGN PATENT DOCUMENTS

| | | |
|---|---|---|
| CA | 2115973 A1 | 9/1994 |
| EP | 0 456 837 A1 | 11/1991 |
| EP | 0 614 868 A1 | 9/1994 |
| EP | 1 055 662 A1 | 11/2000 |
| JP | 53-30688 B | 8/1978 |
| JP | 63-38331 B2 | 7/1988 |
| JP | 3-294238 A | 12/1991 |
| JP | 3-294239 A | 12/1991 |
| JP | 4-217932 A | 8/1992 |
| JP | 8-3093 A | 1/1996 |
| JP | 10-168003 A | 6/1998 |
| JP | 2001-328951 | * 11/2001 |

* cited by examiner

*Primary Examiner*—Paul A. Zucker

(57) ABSTRACT

The object of the present invention is to provide a process in which, when the unsaturated carboxylic acid is produced, or when the unsaturated aldehyde and/or the unsaturated carboxylic acid are produced by carrying out the catalytic gas phase oxidation reaction by using the fixed-bed multitubular reactor which is packed with the molybdenum-containing catalyst, the reaction can be continued for a long time while a high yield is maintained, regardless of where the hot spot portion occurs and also even if the concentration of the raw gas is high. To solve this object, the present invention production process for an unsaturated carboxylic acid is characterized in: a particulate catalysts including, as catalytic components, an oxide and/or a complex oxide including Mo and V, or Mo, Fe and Bi as essential components, and having a hole are used; and a catalyst-packed layer of each reaction tube of the fixed-bed multitubular reactor is divided into at least two reaction zones in a tubular axial direction, wherein the packing of the catalysts is such that the diameters of the holes of the catalysts differ between at least two of the reaction zones.

3 Claims, No Drawings

CATALYTIC GAS PHASE OXIDATION PROCESS

BACKGROUND OF THE INVENTION

A. Technical Field

The present invention relates to a production process for an unsaturated carboxylic acid (e.g. acrylic acid). More particularly, the present invention relates to a process comprising the step of carrying out catalytic gas phase oxidation of an unsaturated aldehyde (e.g. acrolein) with molecular oxygen or a molecular-oxygen-containing gas by using a fixed-bed multitubular reactor which is packed with catalysts, thereby producing an unsaturated carboxylic acid (e.g. acrylic acid).

The present invention also relates to a production process for an unsaturated aldehyde and/or an unsaturated carboxylic acid. More particularly, the present invention relates to a process comprising the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing an unsaturated aldehyde and/or an unsaturated carboxylic acid.

B. Background Art

In the case of carrying out catalytic gas phase oxidation of an unsaturated aldehyde (e.g. acrolein) as a raw material with molecular oxygen or a molecular-oxygen-containing gas by using a fixed-bed multitubular reactor which is packed with catalysts, thereby producing an unsaturated carboxylic acid (e.g. acrylic acid) that correspond to each raw material, or in the case of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with a catalyst, thereby producing an unsaturated aldehyde and/or an unsaturated carboxylic acid that correspond to each raw material, these catalytic gas phase oxidation reactions are accompanied with an extremely exothermic reaction, and therefore a local portion having an extraordinarily high temperature (which may hereinafter be referred to as a hot spot portion) occurs in a catalyst layer.

When the hot spot portion has a high temperature, the hot spot portion excessively causes oxidation reaction to result in lowering a yield, and an excursion reaction is caused if the worst comes to the worst. A catalyst as located at the hot spot portion is exposed to the high temperature, and therefore there is accelerated the deterioration of the catalyst, such as changes of physical properties and chemical properties of the catalyst to result in lowering its activity and the selectivity of the objective product. Particularly, in the case of a molybdenum-containing catalyst (such as molybdenum-bismuth-iron-containing catalysts or molybdenum-vanadium-containing catalysts, hereinafter the same), the composition and properties of the catalyst tend to change due to sublimation of the molybdenum component, and therefore the deterioration extent of the catalyst is large.

The above problems are more striking in the case of carrying out the reaction at a high space velocity or in a high concentration of the raw gas for the purpose of enhancing the productivity of the objective product.

The above problems are explained again. If attention is directed to the entirety of the catalyst layer as packed in the reaction tube, then the catalyst as located at the hot spot portion is more rapidly deteriorated than a catalyst as located at the other portions, and the yield of the objective product is greatly lowered due to longtime use, so its production can be difficult to stably carry out.

In order to cope with such problems, several proposals have hitherto been reported. Examples thereof include: a method that involves diluting a raw-gas-inlet-side catalyst with an inert substance (e.g. JP-B-030688/1978); as a method using a supported catalyst, a method which involves packing a reaction tube with the catalyst in such a manner that the ratio of the catalytic active substance as supported on the support increases from the raw-gas-inlet side toward the raw-gas-outlet side (e.g. JP-A-010802/1995), a method which involves packing a reaction tube with at least two catalysts different as to activity in such a manner that the activity increases from the raw-gas-inlet side toward the raw-gas-outlet side, wherein the catalysts are prepared by changing the kind and/or amount of an alkaline metal as added to the catalysts (e.g. JP-A-336060/2000), a method that involves packing a reaction tube with catalysts in such a manner that the volume of the catalyst as packed in the reaction tube decreases from the raw-gas-inlet side toward the raw-gas-outlet side (e.g. JP-A-241209/1997), and methods as disclosed in such as JP-B-038331/1988, JP-A-294238/1991, JP-A-294239/1991, JP-A-217932/1992, JP-A-003093/1996, and JP-A-168003/1998.

However, in any of these proposals, some extent of improvement is achieved in view of suppressing the temperature of the hot spot portion, but it cannot necessarily be said that the improvement is satisfied in view of the lifetime of the catalyst and the yield of the objective product, and the further improvement is requested under the existing conditions. These problems are remarkable particularly when the reaction is carried out under high-loading conditions (e.g. in a high concentration of the raw gas or at a high space velocity) in the case of using the molybdenum-containing catalyst.

In addition, there is also a problem such that the conventional proposals cannot cope with a method under reaction conditions such that the hot spot portion is formed toward a gas-outlet portion.

SUMMARY OF THE INVENTION

A. Object of the Invention

Accordingly, an object of the present invention is to provide a process in which, when the unsaturated carboxylic acid is produced, or when the unsaturated aldehyde and/or the unsaturated carboxylic acid are produced by carrying out the catalytic gas phase oxidation reaction by using the fixed-bed multitubular reactor which is packed with the molybdenum-containing catalyst, the reaction can be continued for a long time while a high yield is maintained, regardless of where the hot spot portion occurs and also even if the concentration of the raw gas and the space velocity are high.

B. Disclosure of the Invention

The present inventors have diligently studied in order to solve the above-mentioned problems. As a result, they have taken note of a particulate catalyst that has a hole as a catalyst shape. Then, they have come to the thought that: when a catalyst-packed layer of the fixed-bed multitubular reactor is packed with catalysts, the catalyst is packed therein by controlling the diameter of the hole of the catalyst, and thereby the above problems can be solved.

Specifically speaking, they have thought out that: if the catalyst-packed layer is divided into at least two reaction zones, and these reaction zones are packed with the catalysts in such a manner that the diameter of the hole of the catalyst differs between at least two of the reaction zones, the situation is relaxed that the load of the reaction locally rises in at least a portion from the gas-inlet portion to the gas-out-let portion (this is one of causes of the occurrence of the hot spot portion), and the load can be nearly uniform in the entirety of the catalyst-packed layer. Such control of the diameter of the hole of the catalyst has been able to solve the above problems that could not be solved just by using catalysts different as to activity thereby controlling the catalytic activity, as is hitherto carried out.

That is to say, a production process for an unsaturated carboxylic acid, according to the present invention, comprises the step of carrying out catalytic gas phase oxidation of an unsaturated aldehyde with molecular oxygen or a molecular-oxygen-containing gas by using a fixed-bed multitubular reactor which is packed with catalysts, thereby producing the unsaturated carboxylic acid; with the production process being characterized in that: the catalysts include, as catalytic components, an oxide and/or a complex oxide including molybdenum and vanadium as essential components, and are particulate catalysts that have a hole; and a catalyst-packed layer of each reaction tube of the fixed-bed multitubular reactor is divided into at least two reaction zones in a tubular axial direction, wherein the packing of the catalysts is such that the diameters of the holes of the catalysts differ between at least two of the reaction zones.

In the above present invention production process for an unsaturated carboxylic acid, a product as obtained by a process including the step of carrying out catalytic gas phase oxidation of at least one compound selected from the group consisting of propylene, isobutylene, t-butyl alcohol, and methyl t-butyl ether with molecular oxygen or a molecular-oxygen-containing gas can be used as the unsaturated aldehyde.

In addition, a production process for an unsaturated aldehyde and/or an unsaturated carboxylic acid, according to the present invention, comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing the unsaturated aldehyde and/or the unsaturated carboxylic acid which correspond to the raw material; with the production process being characterized in that: the catalysts include, as catalytic components, an oxide and/or a complex oxide including molybdenum, bismuth, and iron as essential components, and are particulate catalysts that have a hole; and a catalyst-packed layer of each reaction tube of the fixed-bed multitubular reactor is divided into at least two reaction zones in a tubular axial direction, wherein the packing of the catalysts is such that the diameters of the holes of the catalysts differ between at least two of the reaction zones.

In the above present invention production process for unsaturated carboxylic acid and production process for an unsaturated aldehyde and/or an unsaturated carboxylic acid, it can be arranged that:

the packing of the catalysts different as to the diameter of the hole should be such that the diameter of the hole decreases from the gas-inlet-side reaction zone of the catalyst-packed layer toward the gas-outlet-side reaction zone thereof in each reaction tube;

the catalyst-packed layer of each reaction tube should be provided with three reaction zones consisting of a first reaction zone, a second reaction zone and a third reaction zone in order from the gas-inlet side, and the diameter of the hole of the catalyst in the second reaction zone should be smaller than that in the first reaction zone, and the outer diameter of the catalyst in the third reaction zone should be smaller than that in the second reaction zone; and the catalysts should be cylindrical catalysts.

These and other objects and the advantages of the present invention will be more fully apparent from the following detailed disclosure.

DETAILED DESCRIPTION OF THE INVENTION

Hereinafter, the production process for an unsaturated aldehyde and/or an unsaturated carboxylic acid and the production process for an unsaturated carboxylic acid (which may hereinafter be referred to as the present invention production process), according to the present invention, are explained in detail. However, the scope of the present invention is not limited to these explanations, and details other than the following examples can fitly be changed and carried out in such a range as not to hinder the objects of the present invention.

Incidentally, unless otherwise noted in the present specification below, described are the explanations relating to both the inventions, namely the present invention production process for an unsaturated aldehyde and/or an unsaturated carboxylic acid, and the present invention production process for an unsaturated carboxylic acid. In addition, of both these inventions, the catalytic gas phase oxidation in the former production process may be referred to as "the former-step reaction", and the catalytic gas phase oxidation in the latter production process may be referred to as "the latter-step reaction". Carrying out this former-step reaction or this latter-step reaction means carrying out the corresponding former or latter production process.

The present invention production process for an unsaturated aldehyde and/or an unsaturated carboxylic acid comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing the unsaturated aldehyde and/or the unsaturated carboxylic acid which correspond to the raw material, and it is important for the production process that: the catalysts (which may hereinafter be referred to as "catalysts A") include, as catalytic components, an oxide and/or a complex oxide including molybdenum, bismuth, and iron as essential components, and are particulate catalysts that have a hole; and a catalyst-packed layer of each reaction tube of the fixed-bed multitubular reactor is divided into at least two reaction zones in a tubular axial direction, wherein the packing of the catalysts is such that the diameters of the holes of the catalysts differ between at least two of the reaction zones.

The present invention production process for an unsaturated carboxylic acid comprises the step of carrying out catalytic gas phase oxidation of an unsaturated aldehyde with molecular oxygen or a molecular-oxygen-containing gas by using a fixed-bed multitubular reactor which is packed with catalysts, thereby producing the unsaturated carboxylic acid, and it is important for the production process in that: the catalysts (which may hereinafter be referred to as "catalysts B") include, as catalytic components, an oxide and/or a complex oxide including molybdenum and vanadium as essential components, and are particulate catalysts that have a hole; and a catalyst-packed layer of each reaction tube of the fixed-bed multitubular reactor is divided into at least two reaction zones in a tubular axial direction, wherein the packing of the catalysts is such that the diameters of the holes of the catalysts differ between at least two of the reaction zones.

In the above present invention production process for an unsaturated carboxylic acid, the unsaturated aldehyde as obtained by the aforementioned present invention production process for an unsaturated aldehyde and/or an unsaturated carboxylic acid can be used as the raw unsaturated aldehyde. That is to say, subsequently to carrying out the aforementioned present invention production process for an unsaturated aldehyde and/or an unsaturated carboxylic acid, the above present invention production process for an unsaturated carboxylic acid is carried out. Thereby, acrolein and/or methacrolein are obtained as the unsaturated aldehyde corresponding to at least one compound which is used as the raw compound and selected from the group consisting of propylene, isobutylene, t-butyl alcohol, and methyl t-butyl ether, and then acrylic acid and/or methacrylic acid can be produced as the unsaturated carboxylic acid corresponding to the above unsaturated aldehyde.

The catalysts as used in the present invention (e.g. the catalysts A and catalysts B, hereinafter the same) may be molded catalysts as obtained by molding only a catalytic component into a definite shape, or supported catalysts as obtained by supporting a catalytic component on any inert support having a definite shape, or catalysts which comprise a combination of these molded catalyst and supported catalyst.

As to the catalytic components, used for the above catalysts A, which include molybdenum, bismuth, and iron as essential components, any catalyst can be used if the use thereof makes it possible to produce the unsaturated aldehyde and/or unsaturated carboxylic acid corresponding to the following raw material by the catalytic gas phase oxidation reaction of at least one compound selected from the group consisting of propylene, isobutylene, t-butyl alcohol, and methyl t-butyl ether as a raw material. However, favorably used are an oxide and/or a complex oxide of a general formula (1) below:

$$Mo_aW_bBi_cFe_dA^1_eB^1_fC^1_gD^1_hE^1_iO_x \qquad (1)$$

(where: Mo is molybdenum; W is tungsten; Bi is bismuth; Fe is iron; $A^1$ is at least one element selected from among cobalt and nickel; $B^1$ is at least one element selected from among sodium, potassium, rubidium, cesium, and thallium; $C^1$ is at least one element selected from among boron, phosphorus, chrome, manganese, zinc, arsenic, niobium, tin, antimony, tellurium, cerium, and lead; $D^1$ is at least one element selected from among silicon, aluminum, titanium, and zirconium; E1 is at least one element selected from among alkaline earth metals; and O is oxygen; and further, a, b, c, d, e, f, g, h, i, and x denote atomic ratios of Mo, W, Bi, Fe, $A^1$, $B^1$, $C^1$, $D^1$, $E^1$, and O respectively; and in the case of a=12, the following inequalities are satisfied: $0 \leq b \leq 5$; $0.1 \leq c \leq 10$; $0.1 \leq d \leq 20$; $1 \leq e \leq 20$; $0.001 \leq f \leq 5$; $0 \leq g \leq 10$; $0 \leq h \leq 30$; and $0 \leq i \leq 5$; and x is a numerical value as determined by the oxidation state of each element).

As to the catalytic components, used for the above catalysts B, which include molybdenum and vanadium as essential components, any catalyst can be used if the use thereof makes it possible to produce the unsaturated carboxylic acid by the catalytic gas phase oxidation reaction of the unsaturated aldehyde. However, favorably used are an oxide and/or a complex oxide of a general formula (2) below:

$$Mo_jV_kA^2_lB^2_mC^2_nD^2_pO_y \qquad (2)$$

(where: Mo is molybdenum; V is vanadium; $A^2$ is niobium and/or tungsten; $B^2$ is at least one element selected from among chrome, manganese, iron, cobalt, nickel, copper, zinc, and bismuth; $C^2$ is at least one element selected from among tin, antimony, and tellurium; $D^2$ is at least one element selected from among alkaline metals; and O is oxygen; and further, j, k, l, m, n, p, and y denote atomic ratios of Mo, V, $A^2$, $B^2$, $C^2$, $D^2$, and O respectively; and in the case of j=12, the following inequalities are satisfied: $1 \leq k \leq 14$, $0 < l \leq 12$; $0 < m \leq 10$; $0 \leq n \leq 10$; $0 \leq p \leq 5$; and y is a numerical value as determined by the oxidation state of each element).

There is no especial limitation on starting materials for the above various catalytic components, which the catalysts as used in the present invention include. Ammonium salts, nitrates, carbonates, chlorides, sulfates, hydroxides, organic acid salts, and oxides of metal elements as generally used for this kind of catalyst or a mixture thereof in combination may be used, but the ammonium salts and nitrates are favorably used.

A liquid of a blend of starting materials (starting-material-blended liquid) may be prepared by a process as generally used for this kind of catalyst. For example, the above starting materials are blended together with water in order thereby preparing an aqueous solution or slurry. However, when at least two aqueous solutions or slurries are prepared depending upon the kind of the starting material, these may be blended together in order. There is no especial limitation on conditions for blending the starting materials (e.g. blending order, temperature, pressure, and pH).

The starting-material-blended liquid as obtained in this way is dried by various methods, thus preparing a dried product (that may be referred to as a catalyst precursor, hereinafter the same). Examples of the methods include a drying method by heating, and a drying method under reduced pressure. Of the above, as to the heating method for obtaining the dried product and the form of the dried product, for example, a powdery dried product may be obtained with such as a spray dryer and a drum dryer, or a blockish or flaky dried product may be obtained by heating under a gas stream with such as a box-type dryer or a tunnel-type dryer. As to the heating method for obtaining the dried product, there is also a case where: the starting-material-blended liquid is evaporated to dryness (concentrated to dryness) to obtain a cake solid, and the above heat treatment of this solid is further carried out. On the other hand, as to the drying method under reduced pressure and the form of the dried product, for example, a blockish or powdery dried product may be obtained by using such as a vacuum dryer.

The dried product as obtained is subjected to a pulverization step or a classification step for obtaining a powder having an appropriate particle diameter when the occasion demands, and then it is transferred into a subsequent molding step. In addition, the dried product as obtained may be calcined before being transferred into the molding step.

There is no especial limitation on the method for molding the catalysts if it is a method that can form particulate catalysts (including supported catalysts) that have a hole, and hitherto publicly known methods are adoptable. Examples thereof include an extrusion-molding method (extrusion-molding machine), a tabletting method, Marumerizer method, an impregnating method, an evaporation-to-dryness method, and a spraying method.

In the case of molding the dried product to be a precursor of the catalytic component in the molding step (the molding includes supporting the dried product on a support), such as liquid binders can be used.

Incidentally, in the case of obtaining the catalysts as used in the present invention, a method (e.g. evaporation-to-dryness method or spraying method) that involves: using the starting-material-blended liquid without drying it; and absorbing the above liquid on a desirable support or coating the above liquid onto a desirable support, thereby supporting catalytic components on the support is also adaptable in addition to the above-mentioned production methods. Accordingly, examples of the method for supporting the catalytic components on the support include a method for supporting the above-mentioned dried product, and besides, a method for supporting the starting-material-blended liquid itself.

There is no especial limitation on the above liquid binders, but usable are binders as generally used for the molding and supporting of this kind of catalyst. Specific examples of the usable binders include: water; and besides, organic compounds, such as ethylene glycol, glycerin, propionic acid, benzyl alcohol, propyl alcohol, poly(vinyl alcohol), and phenol; and nitric acid, and silca sol. In addition, these may be used either alone respectively or in combinations with each other.

In the case of obtaining the catalysts as used in the present invention, usable are various substances (e.g. molding assistants for enabling enhancement of the moldability, reinforcements for enhancing the catalyst strength, and substances that are generally used as pore-forming agents for forming moderate pores in the catalyst) as used for these aimed effects in a general production of catalysts. Examples of these various substances include stearic acid, maleic acid, ammonium nitrate, ammonium carbonate, graphite, starch, cellulose, silica, alumina, glass fibers, silicon carbide, and silicon nitride, and favorable are substances that do not have bad influence on the catalyst performance (e.g. activity, and selectivity of the objective product) by the addition. These various substance can be used, for example, by admixing them to the above liquid binder or starting-material-blended liquid. In the case where the amount of the above substances as added is in excess, there is a case where the physical strength of the catalysts is remarkably lowered, and therefore it is favorable to add them in such an amount as does not lower the physical strength of the catalysts to such an extent that the catalysts cannot be practically used as industrial catalysts.

The catalysts as used in the present invention are particulate catalysts that have a hole. The shape of the hole may be either a penetrated shape or a concave shape including the bottom, but the penetrated hole is favorable.

There is no especial limitation on the shape of the above catalysts if they are particulate, but specific examples thereof favorably include a spherical shape and a column shape (pellet shape). Needless to say, in the case of the spherical shape, the shape of the catalysts is not necessarily a real sphere, but may be substantially a spherical shape. The column shape is also similar to this. Of the above, the column shape is more favorable. Incidentally, in the case of the spherical shape, if the sphere is a real sphere, the outer diameter of the catalyst is a diameter of the corresponding sphere. However, if the sphere is not a real sphere, the average value of the longest outer diameter and the shortest outer diameter is treated as the outer diameter D1 of the catalyst. In the case of the column shape, if its cross section has a real circular shape, the outer diameter of the catalyst is a diameter of the corresponding real circle. However, if it does not have a real circular shape, the average value of the longest outer diameter and the shortest outer diameter is treated as the outer diameter D1 of the catalyst. Incidentally, the outer diameter of the catalyst means the "outer diameter D1" as explained above in the present specification.

There is no especial limitation on the outer diameter D1, but it is favorably in the range of 3 to 15 mm, more favorably 4 to 10 mm.

There is no especial limitation on the opening shape of the hole, but specific examples thereof favorably include a circular shape and an elliptic shape. In the case of the circular shape, the shape is not necessarily a real circular shape, but may be substantially a circular shape. Incidentally, in the case of the circular shape, if the shape is a real circular shape, the diameter of the hole of the catalyst is a diameter of the corresponding real circle. However, if the shape is not a real circular shape, the average value of the longest diameter of the hole and the shortest diameter of the hole is treated as the diameter D2 of the hole of the catalyst. It is also similar to this in the case of the elliptic shape, and the average value of the longest diameter of the hole and the shortest diameter of the hole is treated as the diameter D2 of the hole of the catalyst. Incidentally, the diameter of the hole of the catalyst means the "diameter D2 of the hole" as explained above in the present specification.

There is no especial limitation on the diameter D2 of the hole, but it is favorably in the range of $0.1 \times D1$ to $0.7 \times D1$, more favorably $0.2 \times D1$ to $0.6 \times D1$, still more favorably $0.3 \times D1$ to $0.6 \times D1$. However, when the diameter D2 of the hole is unnecessarily increased, there are cases where: the thickness of the catalyst T ($T=(D1-D2)/2$) is decreased, and the physical strength of the catalyst is lowered. Therefore, it is desirable that the diameter D2 of the hole is selected from among values that are in such an extent that the catalyst can be practically used as an industrial catalyst.

From the above, the catalysts as used in the present invention are most favorably catalysts of which the particle shape of the outer diameter is circular, and cylindrical (ring-shaped) catalysts of which the opening shape is circular along the axis center and which have a penetrated hole (which is also referred to as hollow cylindrical catalysts, hereinafter the same).

In the case of the cylindrical (ring-shaped) catalysts, the height L of the cylindrical shape is favorably in the range of $0.5 \times D1$ to $2.0 \times D1$, more favorably $0.7 \times D1$ to $1.5 \times D1$.

In the case of the supported catalysts, supports having a hole are used as the support. There is no especial limitation on the kind of material of the support itself, and usable is any support that is usually usable in a production of catalysts for the catalytic gas phase oxidation reaction. Specific examples of the usable support include supports having a definite shape and including such as alumina, silica, silica-alumina, titania, magnesia, silica-magnesia, silica-magnesia-alumina, silicon carbide, silicon nitride, and zeolite.

In the case of the supported catalysts, the supporting ratio of the catalyst components is fitly determined so as to obtain the optimum activity and selectivity in consideration of such as the conditions of the oxidation reaction, and the activity and the strength of the catalysts. However, as to the catalysts A, the supporting ratio is favorably in the range of 5 to 95 mass %, more favorably 20 to 90 mass %, and, as to the catalysts B, the supporting ratio is favorably in the range of 10 to 70 mass %, more favorably 15 to 50 mass %. As is mentioned below, in the present invention, the catalyst-packed layer of each reaction tube of the fixed-bed multi-tubular reactor is divided into at least two reaction zones in a tubular axial direction in proportion to the size of the diameter of the hole. However, the supporting ratio of the catalyst components may differ between the respective reaction zones. Herein, the supporting ratio is defined as a value that is obtained from the following equation:

supporting ratio (mass %)=[(mass of catalyst as obtained (g)−mass of support as used (g))/mass of catalyst as obtained (g)]×100.

There is no especial limitation on the heat-treatment conditions (so-called calcination conditions) during the preparation of the catalysts, either. Applicable are calcination conditions that are generally adopted in the production of this kind of catalyst.

As to the catalysts A, the heat-treatment temperature is favorably in the range of 350 to 600° C., more favorably 400 to 550° C., and the heat-treatment time is favorably in the range of 1 to 10 hours.

As to the catalysts B, the heat-treatment temperature is favorably in the range of 350 to 450° C., more favorably 380 to 420° C., and the heat-treatment time is favorably in the range of 1 to 10 hours. In the present invention, the heat-treatment temperature of the catalyst as packed in each reaction zone may be different from that in another reaction zone.

In the present invention production process, it is important to arrange that: the catalyst-packed layer of each reaction tube of the fixed-bed multitubular reactor as used in the reaction should be divided into at least two reaction zones in a tubular axial direction, and at least two of the these reaction zones should be packed with the catalysts different as to the diameter of the hole of the catalyst. That is to say, it is important that the packing of the catalysts is such that the diameters of the holes of the catalyst differ between at least two of the reaction zones.

More specifically speaking of the modes for packing the above catalysts in the fixed-bed multitubular reactor as used in the present invention, examples as to the diameter of the hole of the catalyst includes: a packing mode in such a manner that the diameter of the hole of the catalyst decreases from the gas-inlet-side reaction zone toward the gas-outlet-side reaction zone; and a packing mode in such a manner that: from the gas-inlet-side reaction zone toward the gas-outlet-side reaction zone, the diameter of the hole of the catalyst once increases, but the diameter of the hole of the catalyst in the reaction zone nearest to the gas outlet is smaller than that of the catalyst in the reaction zone nearest to the gas inlet, but there is no especial limitation thereto. As to the latter packing mode, for example, in the case of providing three reaction zones consisting of a first reaction zone, a second reaction zone and a third reaction zone in order from the gas-inlet side toward the gas-outlet side, examples thereof include a mode such that: the diameter of the hole of the catalyst in the second reaction zone is larger than that in the first reaction zone; and the diameter of the hole of the catalyst in the third reaction zone is smaller than that in the second reaction zone; and the diameter of the hole of the catalyst in the third reaction zone is smaller than that in the first reaction zone.

There is no especial limitation on the outer diameter of the catalyst as to the mode for packing the above catalysts in the present invention. Between any two reaction zones adjacent to each other, the outer diameter of the catalyst as packed in the gas-outlet-side reaction zone is either identical with or different from that as packed in the gas-inlet-side reaction zone. However, favorable is a mode such that: the outer diameter of the catalyst as packed in the reaction zone nearest to the gas outlet is smaller than that of the catalyst as packed in the reaction zone nearest to the gas inlet, and more favorable is a mode such that: the outer diameter of the catalyst as packed in the reaction zone nearest to the gas outlet is smaller than that of the catalyst as packed in the reaction zone nearest to the gas inlet, and between any two reaction zones adjacent to each other, the outer diameter of the catalyst as packed in the gas-outlet-side reaction zone is not larger than (namely, smaller than or identical with) that as packed in the gas-inlet-side reaction zone. For example, in the case of providing three reaction zones consisting of a first reaction zone, a second reaction zone and a third reaction zone in order from the gas-inlet side toward the gas-outlet side, the following mode may be applied: a mode such that the outer diameter of the catalyst decreases in order from the first reaction zone toward the third reaction zone; a mode such that: the outer diameter of the catalyst in the second reaction zone is smaller than that in the first reaction zone, and that in the second reaction zone is identical with that in third reaction zone; a mode such that: the outer diameter of the catalyst in the first reaction zone is identical with that in second reaction zone, and that in the third reaction zone is smaller than that in the second reaction zone; a mode such that: the outer diameter of the catalyst in the second reaction zone is larger than that in the first reaction zone, and that in the third reaction zone is smaller than that in the second reaction zone, and that in the third reaction zone is smaller than that in the first reaction zone; or a mode such that: the outer diameter of the catalyst in the second reaction zone is smaller than that in the first reaction zone, and that in the third reaction zone is larger than that in the second reaction zone, and that in the third reaction zone is smaller than that in the first reaction zone. Incidentally, the combination of the mode of the diameter of the hole of the catalyst and the mode of the catalyst outer diameter as mentioned above can fitly be set and changed, and then carried out, and there is no especial limitation thereto.

There is no especial limitation on the number of the reaction zones in the catalyst-packed layer. However, industrially, the aimed effect can be obtained sufficiently by adjusting the number to about 2 or about 3. In addition, as to the dividing ratio of the catalyst-packed layer (ratio of the length of the catalyst-packed layer in each reaction zone), its optimum value depends upon such as the conditions of the oxidation reaction, and the composition, shape, and size of the catalyst as packed in each layer. Therefore, the ratio cannot be specified sweepingly. The ratio may fitly be selected so as to obtain the optimum activity and selectivity as a whole.

The shape of the catalysts as packed in each reaction zone may be identical with or different from each other (e.g. gas-inlet side: spherical catalysts, and gas-outlet side: column-shaped catalysts). It is arranged that the catalysts having the identical shape should be usually packed therein.

As is in the present invention, the effect of obtaining the high activity and the high selectivity of the objective product is caused by using the particulate catalysts that have the hole. Then, if the catalysts are packed in such a manner that the diameters of the holes of the catalysts differ between at least two of the reaction zones as is shown in the present invention, then, when the unsaturated aldehyde and/or the unsaturated carboxylic acid are produced, or the unsaturated carboxylic acid is produced by carrying out the catalytic gas phase oxidation reaction by using the fixed-bed multitubular reactor which is packed with the molybdenum-containing catalyst, the reaction can be continued for a long time while a high yield is maintained, regardless of where the hot spot portion occurs. In addition, only if a method that involves controlling the catalytic activity conventionally by using the catalysts different as to the activity is carried out, there have been problems such that the lifetime of the catalysts extremely shortens particularly in the case where the concentration of the raw gas and the space velocity are high. However, if the present invention production process is used, the reaction can be continued for a long time while a high yield is maintained, even if the concentration of the raw gas is high, and regardless of where the hot spot portion occurs.

More specifically speaking of the modes for packing the catalysts in the fixed-bed multitubular reactor as used in the present invention, as to the packing of the above-mentioned catalysts different as to the diameter of the hole of the catalyst, the first favorable mode is the packing of the catalysts such that the diameter of the hole of the catalyst decreases from the gas-inlet-side reaction zone of the catalyst-packed layer toward the gas-outlet-side reaction zone thereof in each reaction tube. That is to say, the above packing is a mode such that: the diameter of the hole of the catalyst as packed in the reaction zone nearest to the gas outlet is smaller than that of the catalyst as packed in the reaction zone nearest to the gas inlet, and between two reaction zones adjacent to each other, the diameter of the hole of the catalyst as packed in the gas-outlet-side reaction zone is not larger than (namely, smaller than or identical with) that as packed in the gas-inlet-side reaction zone. For example, in the case of providing three reaction zones consisting of a first reaction zone, a second reaction zone and a third reaction zone in order from the gas-inlet side toward the gas-outlet side, the following mode as to the diameter of the hole of the catalyst as packed in each reaction zone may be applied: a mode such that the diameter of the hole of the catalyst as packed in the each reaction zone decreases in order from the first reaction zone toward the third reaction zone; a mode such that: the diameter of the hole of the catalyst in the second reaction zone is smaller than that in the first reaction zone, and that in the second reaction zone is identical with that in third reaction zone; or a mode such that: the diameter of the hole of the catalyst in the first reaction zone is identical with that in second reaction zone, and that in the third reaction zone is smaller than that in the second reaction zone. The first favorable mode generally has effects such that: the deterioration of the catalyst as located at the hot spot portion that occurs near the gas-inlet side is suppressed, and the high selectivity of the objective product is obtained.

In the first favorable mode, the same mode as of the above-mentioned various packing modes can be adopted for the outer diameter of the catalyst as packed in each reaction zone.

Incidentally, in the first favorable mode, the combination of the mode of the diameter of the hole of the catalyst and the mode of the catalyst outer diameter as mentioned above can fitly be set and changed, and then carried out, and there is no especial limitation thereto.

More specifically speaking of the modes for packing the catalysts in the fixed-bed multitubular reactor as used in the present invention, the second favorable mode is such that: in each reaction tube, its catalyst-packed layer is provided with three reaction zones consisting of a first reaction zone, a second reaction zone and a third reaction zone in order from the gas-inlet side, wherein: the diameter of the hole of the catalyst in the second reaction zone is smaller than that in the first reaction zone; and the outer diameter of the catalyst in the third reaction zone is smaller than that in the second reaction zone. The second favorable mode generally has effects such that the activity is enhanced in comparison with the above-mentioned packing such that the diameter of the hole of the catalyst decreases from the gas-inlet-side reaction zone of the catalyst-packed layer toward the gas-outlet-side reaction zone thereof.

As to the diameter of the hole of the catalyst in the second favorable mode, the diameter of the hole of the catalyst in the third reaction zone may further be smaller than, or identical with, or larger than that in the second reaction zone.

Similarly, as to the outer diameter of the catalyst in the second favorable mode, the outer diameter of the catalyst in the second reaction zone may further be smaller than, or identical with, or larger than that in the first reaction zone.

Incidentally, in the second favorable mode, the combination of the mode of the diameter of the hole of the catalyst and the mode of the catalyst outer diameter as mentioned above can fitly be set and changed, and then carried out, and there is no especial limitation thereto.

In the above various packing modes in the present invention production process, it is favorable that, furthermore, the activity of the catalyst as packed in each of the at least two reaction zones differs from that in another of the at least two reaction zones.

There is no especial limitation on the process for producing the above catalysts different as to the activity, and therefore hitherto publicly known processes are also usable. Specific examples thereof include: a process that involves changing the kind and/or amount of at least one element selected from among alkaline metals (the alkaline metal (Na, K, Rb, and Cs) in the component $B^1$ as mentioned in the catalysts A and the component $D^2$ as mentioned in the catalysts B as used in the present invention); a process that involves changing the supporting ratio; a process that involves changing the calcination temperature; a method that involves changing the dilution ratio; a process that involves changing the particle diameters of the catalysts; and a process that involves a combination of these processes. Of the above, the process that involves the combination is favorable in view of the lifetime of the catalysts and the yield.

As to the mode for packing the catalysts in the case where the at least two reaction zones are packed with the catalysts in the above manner that the activity of the catalyst in each reaction zone differs from that in another reaction zone, and when attention is directed to the activity, examples of the packing mode include: a mode in such a manner that the activity increases in order from the gas-inlet side toward the gas-outlet side; and a mode in such a manner that, from the gas-inlet side toward the gas-outlet side, the activity once decreases and thereafter increases. Favorable is a mode such that the catalysts different as to the activity are packed in such a manner that the activity increases in order from the gas-inlet side of each reaction tube toward the gas-outlet side thereof. That is to say, the mode is such that the catalyst having the lowest activity is packed on the gas-inlet side, and the catalyst having the highest activity is packed on the gas-outlet side. In addition, in the packing mode in such a manner that the activity once decreases and thereafter increases from the gas-inlet side toward the gas-outlet side, the ratio of the layer length of the packed catalyst having the higher activity on the gas-inlet side is favorably not more than 50%, more favorably not more than 20%, still more favorably not more than 10%, relative to the total catalyst layer length.

If the at least two catalysts different as to the activity are arranged in the above way, the heat accumulation is suppressed at the hot spot portion, and the objective product can be obtained stably for a long time with high selectivity.

When the catalysts are packed into the catalyst-packed layer of each reaction tube, the catalysts as diluted with an inert substance can also be packed into each reaction zone.

As to the present invention production process for an unsaturated aldehyde and/or an unsaturated carboxylic acid, there is no especial limitation on the specific production process which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas, thereby producing the unsaturated aldehyde and/or the unsaturated carboxylic acid which correspond to the above raw material, except for using the present invention catalysts (catalysts A) as catalysts. This production process can be carried out with generally used apparatuses, by generally used methods, and under generally used conditions.

In the present invention production process for an unsaturated carboxylic acid, there is no especial limitation on the specific production process which comprises the step of carrying out catalytic gas phase oxidation of an unsaturated aldehyde (e.g. acrolein) with molecular oxygen or a molecular-oxygen-containing gas, thereby producing the unsaturated carboxylic acid (e.g. acrylic acid), except for using the present invention catalysts (catalysts B) as catalysts. This production process can be carried out with generally used apparatuses, by generally used methods, and under generally used conditions.

That is to say, the catalytic gas phase reaction in the present invention production process may be carried out by a conventional one-pass method or recycling method.

The unsaturated aldehyde as mentioned in the present invention production process for an unsaturated carboxylic acid is usually subjected to the catalytic gas phase oxidation in a state of a raw gas containing this unsaturated aldehyde. A mixed gas can be used as the above raw gas, wherein the mixed gas includes, for example, unsaturated aldehydes (e.g. acrolein and methacrolein) and at least one member selected from the group consisting of air, oxygen, water vapor, inert gases, and other various gases.

Applicable as the unsaturated aldehyde as mentioned in the present invention production process for an unsaturated carboxylic acid are acrolein and/or methacrolein in a reaction gas as obtained by carrying out catalytic gas phase oxidation of at least one compound selected from the group consisting of propylene, isobutylene, t-butyl alcohol, and methyl t-butyl ether with molecular oxygen or a molecular-oxygen-containing gas. In the case of the above application, the above reaction gas may be used as it is, or can also be used after adding at least one gas selected from the group consisting of air, oxygen, water vapor, inert gases, and other various gases to the reaction gas when the occasion demands. The above reaction gas as obtained by carrying out the catalytic gas phase oxidation of the above compounds such as the propylene can include such as acrylic acid, methacrylic acid, acetic acid, carbon oxide, propane, the unreacted propylene, the unreacted isobutylene, the unreacted t-butyl alcohol, and the unreacted methyl t-butyl ether as by-products. However, these by-products do no harm to such as performance of the catalysts (catalysts B) as used in the present invention. Examples of the catalysts as used in the case of carrying out the catalytic gas phase oxidation of the above compounds such as the propylene include publicly known catalysts usable in this oxidation, such as molybdenum-containing catalysts (e.g. molybdenum-bismuth-iron-containing catalysts). Specifically, the above-mentioned catalysts A are favorable. In addition, in the case of carrying out the catalytic gas phase oxidation of the above compounds such as the propylene, the present invention production process for an unsaturated aldehyde and/or an unsaturated carboxylic acid is favorable applicable.

As to conditions of the above reaction for carrying out the present invention production process for an unsaturated aldehyde and/or an unsaturated carboxylic acid, exemplified is the reaction as carried out, for example, by bringing a mixed gas into contact with the catalysts (catalysts A) as mentioned in the present invention, in the temperature range of 250 to 450° C. (favorably 270 to 430° C.) under a pressure of 0.1 to 1 MPa at a space velocity of 300 to 5,000 hr$^{-1}$ (STP) (favorably 500 to 3,000 hr$^{-1}$ (STP)), wherein the mixed gas includes: 1 to 15 volume % (favorably 4 to 12 volume %) of at least one compound selected from the group consisting of propylene, isobutylene, t-butyl alcohol, and methyl t-butyl ether as a raw gas; 1 to 30 volume % (favorably 2 to 25 volume %) of oxygen (molecular oxygen); 0 to 50 volume % (favorably 0 to 20 volume %) of water vapor; and 20 to 80 volume % (favorably 40 to 70 volume %) of an inert gas (e.g. nitrogen gas, and carbon dioxide gas) as a diluent.

As to conditions of the above reaction for carrying out the present invention production process for an unsaturated carboxylic acid, exemplified is the reaction as carried out, for example, by bringing a mixed gas into contact with the catalysts (catalysts B) as mentioned in the present invention, in the temperature range of 200 to 400° C. (favorably 220 to 380° C.) under a pressure of 0.1 to 1 MPa at a space velocity of 300 to 10,000 hr$^{-1}$ (STP) (favorably 500 to 5,000 hr$^{-1}$ (STP)), wherein the mixed gas includes: 1 to 15 volume % (favorably 4 to 12 volume %) of an unsaturated aldehyde; 0.5 to 25 volume % (favorably 2 to 20 volume %) of oxygen (molecular oxygen); 0 to 30 volume % (favorably 0 to 25 volume %) of water vapor; and 20 to 80 volume % (favorably 50 to 70 volume %) of an inert gas (e.g. nitrogen gas, and carbon dioxide gas).

The present invention production process can give particularly remarkably favorable results in comparison with conventional processes under high-loading reaction conditions that aim at enhancing the productivity, for example, under conditions where: the concentration of the raw gas is higher or the space velocity is higher. Particularly, the object of the present invention can be achieved even if a high-concentration raw gas such as has a raw-gas concentration of not smaller than 7 volume % (more severely not smaller than 9 volume %) is used.

(Effects and Advantages of the Invention):

When the unsaturated aldehyde and/or the unsaturated carboxylic acid are produced by carrying out the catalytic gas phase oxidation reaction by using the fixed-bed multi-tubular reactor which is packed with the molybdenum-containing catalyst, or when the unsaturated carboxylic acid such as acrylic acid is produced by carrying out the catalytic gas phase oxidation reaction by using the fixed-bed multi-tubular reactor which is packed with the molybdenum-vanadium-containing catalyst, the present invention enables continuation of the reaction for a long time while a high yield is maintained, regardless of where the hot spot portion occurs and also even if the concentration of the raw gas is high.

DETAILED DESCRIPTION OF THE PREFERRED EMBODIMENTS

Hereinafter, the present invention is more specifically illustrated by the following examples of some preferred embodiments. However, the present invention is not limited to these examples in any way. Hereinafter, there are cases where the units "part(s) by mass" and "liter(s)" are simply abbreviated to "part(s)" and "L" respectively for the sake of convenience.

The former-step reaction was carried out in the following way.

Incidentally, each of the conversion, selectivity, and yield in the former-step reaction is defined as follows.

Conversion (mol %)=(mols of reacted raw compound/mols of supplied raw compound)×100

Selectivity (mol %)=(mols of produced unsaturated aldehyde and unsaturated carboxylic acid/mols of reacted raw compound)×100

Yield (mol %)=(mols of produced unsaturated aldehyde and unsaturated carboxylic acid/mols of supplied raw compound)×100

The catalysts as used for carrying out the former-step reaction were produced in the following way.

PRODUCTION EXAMPLE 1-1

(Preparation of Catalyst (1-1)):

While 10,000 parts of pure water was heat-stirred, 1,500 parts of ammonium molybdate and 96 parts of ammonium paratungstate were dissolved thereinto, and 319 parts of 20 mass % silica sol was further added thereto. To this mixed liquid, a liquid as obtained by dissolving 824 parts of cobalt nitrate, 286 parts of iron nitrate, and 4.3 parts of potassium nitrate into 1,000 parts of pure water was dropwise added under vigorously stirred conditions. Subsequently, a liquid as obtained by dissolving 343 parts of bismuth nitrate into an aqueous solution was dropwise added thereto under vigorously stirred conditions to thus prepare a suspension, wherein the aqueous solution was obtained by adding 325 parts of concentrated nitric acid to 500 parts of pure water. Next, the suspension was dried with a drum dryer, thus obtaining a dried product. This dried product was pulverized to thus obtain a powder having a particle diameter of not larger than 500 µm. To this powder, a graphite powder was added as a molding assistant in such a manner that the ratio of the graphite powder would be 3 mass %, and they were mixed for 10 minutes. Thereafter, the resultant mixture was molded by using a tablet machine into a cylindrical shape (ring shape) of 6.0 mm in outer diameter, 2.0 mm in diameter of the hole, and 4.5 mm in height. Next, the resultant molded structure was calcined under a stream of air at 450° C. for 5 hours, thus obtaining a catalyst (1-1). The composition of metal elements in this catalyst except for oxygen was as follows:

$Mo_{12}W_{0.5}Co_4Bi_1Fe_1Si_{1.5}K_{0.06}$ catalyst (1-1):

As to the catalyst (1-1), the composition of the catalyst, the size of the catalyst, and the molding method, and the calcination temperature are summarized in Table 1.

PRODUCTION EXAMPLE 1-2

(Preparation of Catalyst (1-2)):

A catalyst (1-2) was obtained in the same way as of Production Example 1-1 except for carrying out the molding in such a manner that the size of the catalyst would be 6.0 mm in outer diameter, 3.0 mm in diameter of the hole, and 4.5 mm in height.

As to the catalyst (1-2), the composition of the catalyst, the size of the catalyst, the molding method, and the calcination temperature are summarized in Table 1.

PRODUCTION EXAMPLE 1-3

(Preparation of Catalyst (1-3)):

While 10,000 parts of pure water was heat-stirred, 1,500 parts of ammonium molybdate and 96 parts of ammonium paratungstate were dissolved thereinto, and 425 parts of 20 mass % silica sol was further added thereto. To this mixed liquid, a liquid as obtained by dissolving 1,030 parts of cobalt nitrate, 618 parts of nickel nitrate, 343 parts of iron nitrate, and 5.7 parts of potassium nitrate into 1,000 parts of pure water was dropwise added under vigorously stirred conditions. Subsequently, a liquid as obtained by dissolving 446 parts of bismuth nitrate into an aqueous solution was dropwise added thereto under vigorously stirred conditions, wherein the aqueous solution was obtained by adding 325 parts of concentrated nitric acid to 500 parts of pure water. Then, the suspension as produced was heat-stirred, and thereby the major part of the water was evaporated, thus obtaining a cake solid. The cake solid as obtained was heat-treated with a box-type dryer, thus obtaining a blockish dried product. This dried product was pulverized to thus obtain a powder. To this powder, 50 mass % aqueous ammonium nitrate solution was added as a binder, and the resultant mixture was kneaded for 1 hour. Thereafter, the mixture was extrusion-molded into a cylindrical shape (ring shape) of 5.5 mm in outer diameter, 2.0 mm in diameter of the hole, and 6.1 mm in height. Next, the resultant molded structure was calcined under a stream of air at 480° C. for 5 hours, thus obtaining a catalyst (1-3). The composition of metal elements in this catalyst except for oxygen was as follows:

$Mo_{12.0}W_{0.5}Co_5Ni_3Bi_{1.3}Fe_{1.2}Si_2K_{0.08}$ catalyst (1-3):

As to the catalyst (1-3), the composition of the catalyst, the size of the catalyst, the molding method, and the calcination temperature are summarized in Table 1.

PRODUCTION EXAMPLES 1-4 TO 1-8

(Preparation of Catalysts (1-4) to (1-8)):

Catalysts (1-4) to (1-6) were obtained in the same way as of Production Example 1-3 except for carrying out the molding in such a manner that the size of the catalyst would be that as listed in Table 1.

As to all the catalysts (1-4) to (1-6), the composition of metal elements in the catalyst except for oxygen was each the same as of the catalyst (1-3).

A catalyst (1-7) was obtained in the same way as of Production Example 1-3 except that the amount of the potassium nitrate as used was changed to 3.6 parts in Production Example 1-3. In addition, a catalyst (1-8) was obtained in the same way as of Production Example 1-3 except for: using 9.7 parts of cesium nitrate instead of the potassium nitrate, and carrying out the molding in such a manner that the size of the catalyst would be that as listed in Table 1.

As to the catalysts (1-7) and (1-8), the composition of metal elements in the catalyst except for oxygen was as follows:

$Mo_{12}W_{0.5}Co_5Ni_3Bi_{1.3}Fe_{1.2}Si_2K_{0.05}$;  catalyst (1-7):

and $Mo_{12}W_{0.5}Co_5Ni_3Bi_{1.3}Fe_{1.2}Si_2Cs_{0.07}$.  catalyst (1-8):

As to the catalysts (1-4) to (1-8), the composition of the catalyst, the size of the catalyst, the molding method, and the calcination temperature are summarized in Table 1.

PRODUCTION EXAMPLE 1-9

(Preparation of Catalyst (1-9)):

While 10,000 parts of pure water was heat-stirred, 1,500 parts of ammonium molybdate and 382 parts of ammonium paratungstate were dissolved thereinto, and 213 parts of 20 mass % silica sol was further added thereto. To this mixed liquid, a liquid as obtained by dissolving 1,442 parts of cobalt nitrate, 429 parts of ferric nitrate, and 83 parts of cesium nitrate into 1,000 parts of pure water was dropwise added under vigorously stirred conditions. Subsequently, a liquid as obtained by dissolving 515 parts of bismuth nitrate into an aqueous solution was dropwise added thereto under vigorously stirred conditions, wherein the aqueous solution was obtained by adding 325 parts of concentrated nitric acid to 500 parts of pure water. Then, the suspension as produced was heat-stirred, and thereby the major part of the water was evaporated, thus obtaining a cake solid. The cake solid as obtained was heat-treated with a box-type dryer, thus obtaining a blockish dried product. This dried product was pulverized to thus obtain a powder. To this powder, 50 mass % aqueous ammonium nitrate solution was added as a binder, and the resultant mixture was kneaded for 1 hour. Thereafter, the mixture was extrusion-molded into a cylindrical shape (ring shape) of 5.5 mm in outer diameter, 2.0 mm in diameter of the hole, and 6.5 mm in height. Next, the resultant molded structure was calcined under a stream of air at 500° C. for 5 hours, thus obtaining a catalyst (1-9). The composition of metal elements in this catalyst except for oxygen was as follows:

$Mo_{12}W_2Co_7Bi_{1.5}Fe_{1.5}Si_1Cs_{0.6}$.  catalyst (1-9):

As to the catalyst (1-9), the composition of the catalyst, the size of the catalyst, the molding method, and the calcination temperature are summarized in Table 1.

PRODUCTION EXAMPLE 1-10

(Preparation of Catalyst (1-10)):

A catalyst (1-10) was obtained in the same way as of Production Example 1-9 except for carrying out the molding in such a manner that the size of the catalyst would be 5.5 mm in outer diameter, 3.0 mm in diameter of the hole, and 6.5 mm in height. The composition of metal elements in the catalyst (1-10) except for oxygen was the same as of the catalyst (1-9).

As to the catalyst (1-10), the composition of the catalyst, the size of the catalyst, the molding method, and the calcination temperature are summarized in Table 1.

As was shown below, the catalytic gas phase oxidation with regard to the former-step reaction was carried out by using the catalysts as obtained in the above-mentioned production examples.

EXAMPLE 1-1

The catalysts (1-2) and (1-1) were packed into a catalyst-packed layer of a stainless-steel-made reaction tube of 25 mm in inner diameter (as heated with a molten nitrate salt) in this order from its gas-inlet side toward its gas-outlet side in such a manner that: the layer length of the catalyst (1-2) would be 1,000 mm, and the layer length of the catalyst (1-1) would be 2,000 mm, and then a catalytic gas phase oxidation reaction of propylene was carried out by introducing a mixed gas having the following composition at a space velocity of 1,500 hr$^{-1}$ (STP). The reaction was continuously carried out for 4,000 hours, and the results as obtained when 100 hours and 4,000 hours each passed from the beginning of the reaction are listed in Table 2.

Propylene: 6 volume %
Air: 55 volume %
Water vapor: 10 volume %
Nitrogen: 29 volume %

COMPARATIVE EXAMPLE 1-1

A catalytic gas phase oxidation reaction was carried out in the same way as of Example 1-1 except for packing only the catalyst (1-1) in such a manner that its layer length would be 3,000 mm. The reaction was continuously carried out for 4,000 hours, and the results as obtained when 100 hours and 4,000 hours each passed from the beginning of the reaction are listed in Table 2.

COMPARATIVE EXAMPLE 1-2

A catalytic gas phase oxidation reaction was carried out in the same way as of Example 1-1 except for packing only the catalyst (1-2) in such a manner that its layer length would be 3,000 mm. The reaction was continuously carried out for 4,000 hours, and the results as obtained when 100 hours and 4,000 hours each passed from the beginning of the reaction are listed in Table 2.

EXAMPLES 1-2 AND 1-3, AND COMPARATIVE EXAMPLES 1-3

Catalytic gas phase oxidation reactions were carried out in the same way as of Example 1-1 except that: the catalysts were packed as listed in Table 2, and the composition of the mixed gas was changed to the following composition. The reaction was continuously carried out for 4,000 hours, and the results as obtained when 100 hours and 4,000 hours each passed from the beginning of the reaction are listed in Table 2.

Propylene: 7 volume %
Air: 60 volume %
Water vapor: 8 volume %
Nitrogen: 25 volume %

EXAMPLES 1-4 AND 1-5

Catalytic gas phase oxidation reactions were carried out in the same way as of Example 1-1 except that: the catalysts were packed as listed in Table 2, and the composition of the mixed gas was changed to the following composition. The reaction was continuously carried out, and the results as obtained when 100 hours passed from the beginning of the reaction are listed in Table 2.

Propylene: 9 volume %
Air: 75 volume %
Water vapor: 8 volume %
Nitrogen: 8 volume %

EXAMPLE 1-6

The catalysts (1-10) and (1-9) were packed into a catalyst-packed layer of a stainless-steel-made reaction tube of 25 mm in inner diameter (as heated with a molten nitrate salt) in this order from its gas-inlet side toward its gas-outlet side in such a manner that: the layer length of the catalyst (1-10) would be 1,000 mm, and the layer length of the catalyst (1-9) would be 2,000 mm, and then a catalytic gas phase oxidation reaction of isobutylene was carried out by introducing a mixed gas having the following composition at a space velocity of 1,500 hr$^{-1}$ (STP). The reaction was continuously carried out, and the results as obtained when 100 hours passed from the beginning of the reaction are listed in Table 3.

Isobutylene: 6 volume %
Air: 65 volume %
Water vapor: 8 volume %
Nitrogen: 21 volume %

COMPARATIVE EXAMPLE 1-4

A catalytic gas phase oxidation reaction was carried out in the same way as of Example 1-6 except for packing only the catalyst (1-9) in such a manner that its layer length would be 3,000 mm. The reaction was continuously carried out, and the results as obtained when 100 hours passed from the beginning of the reaction are listed in Table 3.

COMPARATIVE EXAMPLE 1-5

A catalytic gas phase oxidation reaction was carried out in the same way as of Example 1-6 except for packing only the catalyst (1-10) in such a manner that its layer length would be 3,000 mm. The reaction was continuously carried out, and the results as obtained when 100 hours passed from the beginning of the reaction are listed in Table 3.

TABLE 1

| Catalyst number | Composition of catalyst | Outer diameter D1 (mm) | Diameter of hole D2 (mm) | Thickness T (mm) | Height L (mm) | Molding method | Calcination temperature (° C.) |
|---|---|---|---|---|---|---|---|
| (1-1) | $Mo_{12}W_{0.5}Co_4Bi_1Fe_1Si_{1.5}K_{0.06}$ | 6.0 | 2.0 | 2.00 | 4.5 | tabletting | 450 |
| (1-2) | ↑ | 6.0 | 3.0 | 1.50 | 4.5 | ↑ | 450 |
| (1-3) | $Mo_{12}W_{0.5}Co_5Ni_3Bi_{1.3}Fe_{1.2}Si_2K_{0.08}$ | 5.5 | 2.0 | 1.75 | 6.1 | extrusion | 480 |
| (1-4) | ↑ | 6.0 | 2.0 | 2.00 | 6.6 | ↑ | 480 |
| (1-5) | ↑ | 7.0 | 2.0 | 2.50 | 7.7 | ↑ | 480 |
| (1-6) | ↑ | 7.0 | 3.0 | 2.00 | 7.7 | ↑ | 480 |
| (1-7) | $Mo_{12}W_{0.5}Co_5Ni_3Bi_{1.3}Fe_{1.2}Si_2K_{0.05}$ | 5.5 | 2.0 | 1.75 | 6.1 | ↑ | 480 |
| (1-8) | $Mo_{12}W_{0.5}Co_5Ni_3Bi_{1.3}Fe_{1.2}Si_2Cs_{0.07}$ | 7.0 | 3.0 | 2.00 | 7.7 | ↑ | 480 |
| (1-9) | $Mo_{12}W_2Co_7Bi_{1.5}Fe_{1.5}Si_1Cs_{0.6}$ | 5.5 | 2.0 | 1.75 | 6.5 | ↑ | 500 |
| (1-10) | ↑ | 5.5 | 3.0 | 1.25 | 6.5 | ↑ | 500 |

TABLE 2

| | Method for packing catalysts (gas-inlet side → gas-outlet side) | Reaction time (hours) | Reaction temperature (° C.) | Conversion of propylene (mol %) | Total yield of acrolein and acrylic acid (mol %) | Total selectivity of acrolein and acrylic acid (mol %) |
|---|---|---|---|---|---|---|
| Example 1-1 | catalyst (1-2)/catalyst (1-1) = 1000 mm/2000 mm | 100 | 315 | 96.5 | 91.8 | 95.1 |
| | | 4000 | 321 | 96.5 | 92.0 | 95.3 |
| Comparative Example 1-1 | catalyst (1-1) = 3000 mm | 100 | 315 | 96.6 | 91.2 | 94.4 |
| | | 4000 | 320 | 96.6 | 91.0 | 94.2 |
| Comparative Example 1-2 | catalyst (1-2) = 3000 mm | 100 | 320 | 96.5 | 91.1 | 94.4 |
| | | 4000 | 331 | 96.5 | 91.3 | 94.6 |
| Example 1-2 | catalyst (1-6)/catalyst (1-4) = 1000 mm/2000 mm | 100 | 315 | 97.9 | 92.4 | 94.4 |
| | | 4000 | 323 | 97.9 | 92.1 | 94.1 |
| Example 1-3 | catalyst (1-6)/catalyst (1-4)/catalyst (1-3) = 1000 mm/1000 mm/1000 mm | 100 | 315 | 98.3 | 92.7 | 94.3 |
| | | 4000 | 319 | 98.4 | 92.9 | 94.4 |
| Comparative Example 1-3 | catalyst (1-5)/catalyst (1-4) = 1000 mm/2000 mm | 100 | 315 | 98.0 | 91.9 | 93.8 |
| | | 4000 | 328 | 97.7 | 91.1 | 93.2 |
| Example 1-4 | catalyst (1-8)/catalyst (1-4) = 1000 mm/2000 mm | 100 | 320 | 97.7 | 91.3 | 93.4 |
| Example 1-5 | catalyst (1-8)/catalyst (1-4)/catalyst (1-7) = 1000 mm/1300 mm/700 mm | 100 | 317 | 98.0 | 91.6 | 93.5 |

TABLE 3

| | Method for packing catalysts (gas-inlet side → gas-outlet side) | Reaction time (hours) | Reaction temperature (° C.) | Conversion of isobutylene (mol %) | Total yield of methacrolein and methacrylic acid (mol %) | Total selectivity of methacrolein and methacrylic acid (mol %) |
|---|---|---|---|---|---|---|
| Example 1-6 | catalyst (1-10)/catalyst (1-9) = 1000 mm/2000 mm | 100 | 340 | 98.0 | 87.6 | 89.4 |
| Comparative Example 1-4 | catalyst (1-9) = 3000 mm | 100 | 340 | 98.2 | 87.0 | 88.6 |
| Comparative Example 1-5 | catalyst (1-10) = 3000 mm | 100 | 345 | 98.0 | 87.1 | 88.9 |

The latter-step reaction was carried out in the following way.

Incidentally, each of the conversion, selectivity, and yield in the latter-step reaction is defined as follows.

Conversion of unsaturated aldehyde (mol %)=(mols of reacted unsaturated aldehyde/mols of supplied unsaturated aldehyde)×100

Selectivity of unsaturated carboxylic acid (mol %)= (mols of produced unsaturated carboxylic acid/ mols of reacted unsaturated aldehyde)×100

Yield of unsaturated carboxylic acid (mol %)=(mols of produced unsaturated carboxylic acid/mols of supplied unsaturated aldehyde)×100

The catalysts as used for carrying out the latter-step reaction were produced in the following way.

PRODUCTION EXAMPLE 2-1

(Preparation of Catalyst (2-1)):

While 20,000 parts of pure water was heat-stirred, 3,000 parts of ammonium molybdate, 547 parts of ammonium metavanadate, and 459 parts of ammonium paratungstate were dissolved thereinto. While 2,000 parts of pure water was separately heat-stirred, 547 parts of copper nitrate trihydrate was dissolved thereinto. The resultant two aqueous solutions were mixed together, and this mixed liquid was evaporated to dryness to obtain a cake solid while the heat-stirring was continued. Thereafter, the solid as obtained was calcined under an atmosphere of air at 380° C. for 5 hours. Subsequently, this calcined product was pulverized to thus obtain a catalytic component powder having a particle diameter of not larger than 500 μm. To the catalytic component powder as obtained, a graphite powder was added in such a manner that the ratio of the graphite powder would be 3 mass %. Then, the resultant mixture was molded by using a tablet machine into a cylindrical shape (ring shape) of 7 mm in outer diameter, 2 mm in diameter of the hole, and 7 mm in height. Next, the resultant molded structure was calcined under an atmosphere of air at 380° C. for 2 hours, thus obtaining a catalyst (2-1). The composition of metal elements in the catalyst (2-1) except for oxygen was as follows:

$Mo_{12}V_{3.3}W_{1.2}Cu_{1.6}$.  catalyst (2-1):

As to the catalyst (2-1), the composition of the catalyst, the size of the catalyst, and the molding method, and the calcination temperature are listed in Table 4.

PRODUCTION EXAMPLE 2-2

(Preparation of Catalyst (2-2)):

A catalyst (2-2) was obtained in the same way as of Production Example 2-1 except for carrying out the molding in such a manner that the diameter of the hole of the catalyst would be 3 mm. The composition of metal elements in the catalyst (2-2) except for oxygen was the same as of the catalyst (2-1).

As to the catalyst (2-2), the composition of the catalyst, the size of the catalyst, and the molding method, and the calcination temperature are listed in Table 4.

PRODUCTION EXAMPLE 2-3

(Preparation of Catalyst (2-3)):

While 20,000 parts of pure water was heat-stirred, 3,000 parts of ammonium molybdate, 547 parts of ammonium metavanadate, and 459 parts of ammonium paratungstate were dissolved thereinto. While 2,000 parts of pure water was separately heat-stirred, 547 parts of copper nitrate trihydrate was dissolved thereinto. The resultant two aqueous solutions were mixed together, and further 62 parts of antimony trioxide was added thereto. The resultant mixed liquid and a silica-alumina support were together put in a ceramic evaporation pan on a warm water bath, wherein the silica-alumina support has a cylindrical shape (ring shape) of 8 mm in outer diameter, 3 mm in diameter of the hole, and 8 mm in height. Then, they were evaporated to dryness under stirred conditions to thus support the catalytic components on the support. Subsequently, this dried support was calcined under an atmosphere of air at 400° C. for 5 hours, thus obtaining a catalyst (2-3). The supporting ratio of the catalyst (2-3) was 20 mass %. The composition of metal elements in the catalyst components of the catalyst (2-3) except for oxygen was as follows:

$Mo_{12}V_{3.3}W_{1.2}Cu_{1.6}Sb_{0.3}$.  catalyst (2-3):

As to the catalyst (2-3), the composition of the catalyst, the size of the catalyst, and the molding method, and the calcination temperature are listed in Table 4.

PRODUCTION EXAMPLES 2-4 AND 2-5

(Preparation of Catalysts (2-4) and (2-5)):

A catalysts (2-4) and a catalyst (2-5) were obtained in the same way as of Production Example 2-3 except for using a silica-alumina support having a cylindrical shape (ring shape) of 7 mm in outer diameter, 2 mm in diameter of the hole, and 7 mm in height, and a silica-alumina support having a cylindrical shape (ring shape) of 6 mm in outer diameter, 2 mm in diameter of the hole, and 6 mm in height, respectively. As to both the catalysts (2-4) and the catalyst (2-5), the supporting ratio was 20 mass %. As to both the catalysts (2-4) and the catalyst (2-5), the composition of metal elements in the catalyst except for oxygen was the same as of the catalyst (2-3).

As to the catalyst (2-4) and the catalyst (2-5), the composition of the catalyst, the size of the catalyst, and the molding method, and the calcination temperature are listed in Table 4.

As was shown below, the catalytic gas phase oxidation with regard to the latter-step reaction was carried out by using the catalysts as obtained in the above-mentioned production examples.

EXAMPLE 2-1

The catalysts (2-2) and (2-1) were packed into a catalyst-packed layer of a stainless-steel-made reaction tube of 25 mm in inner diameter (as heated with a molten nitrate salt) in this order from its gas-inlet side toward its gas-outlet side in such a manner that: the layer length of the catalyst (2-2) would be 1,000 mm, and the layer length of the catalyst (2-1) would be 2,000 mm, and then a catalytic gas phase oxidation reaction of acrolein was carried out by introducing a mixed gas having the following composition at a space velocity of 2,100 hr$^{-1}$ (STP). The reaction was continuously carried out for 4,000 hours, and the results as obtained when 100 hours and 4,000 hours each passed from the beginning of the reaction are listed in Table 5.

Acrolein: 4.5 volume %
Air: 25.0 volume %
Water vapor: 30.0 volume %
Nitrogen: 40.5 volume %

COMPARATIVE EXAMPLE 2-1

A catalytic gas phase oxidation reaction of acrolein was carried out in the same way as of Example 2-1 except for packing only the catalyst (2-1) without using the catalyst (2-2) in such a manner that its layer length would be 3,000 mm. The reaction was continuously carried out for 4,000 hours, and the results as obtained when 100 hours and 4,000 hours each passed from the beginning of the reaction are listed in Table 5.

COMPARATIVE EXAMPLE 2-2

A catalytic gas phase oxidation reaction of acrolein was carried out in the same way as of Example 2-1 except for packing only the catalyst (2-2) without using the catalyst (2-1) in such a manner that its layer length would be 3,000 mm. The reaction was continuously carried out for 4,000 hours, and the results as obtained when 100 hours and 4,000 hours each passed from the beginning of the reaction are listed in Table 5.

EXAMPLE 2-2

As was shown below, a catalytic gas phase oxidation reaction of propylene as a raw compound with regard to the former-step reaction was carried out, and the resultant mixed gas was used to thus carry out a catalytic gas phase oxidation reaction with regard to the latter-step reaction.

(Catalyst for Oxidation of Propylene):

As catalysts for oxidation of propylene, the catalyst (1-4) as obtained in Production Example 1-4 and the catalyst (1-6) as obtained in Production Example 1-6 were used.

(Packing of Catalyst for Oxidation of Propylene):

The catalysts were packed into a catalyst-packed layer of a stainless-steel-made reaction tube of 25 mm in inner diameter (as heated with a molten nitrate salt) in order from its gas-inlet side toward its gas-outlet side in such a manner that: the layer length of the catalyst (1-6) would be 1,000 mm, and the layer length of the catalyst (1-4) would be 2,000 mm.

(Oxidation Reaction of Propylene):

A mixed gas (a) including 7 volume % of propylene (propylene for industrial use (purity: 96%)), 60 volume % of air, 8 volume % of water vapor, and 24.7 volume % of nitrogen was introduced into the reaction tube as packed with the above catalysts (1-4) and (1-6), and then a catalytic gas phase oxidation reaction of propylene was carried out at a space velocity of 1,600 hr$^{-1}$ (STP), thus obtaining a mixed gas (b) including acrolein.

(Oxidation Reaction of Acrolein):

The mixed gas (b) as obtained was introduced into a reaction tube as packed with the catalysts (2-1) and (2-2) in the same way as of Example 2-1, and then a catalytic gas phase oxidation reaction of the acrolein was carried out. The reaction was continuously carried out for 4,000 hours, and the results as obtained when 100 hours and 4,000 hours each passed from the beginning of the reaction are listed in Table 5.

Incidentally, as to the above results in the oxidation reaction of the acrolein, the calculation was carried out on the assumption that no gas other than the acrolein (e.g. propylene, propane, acrylic acid, and acetic acid) in the mixed gas (b) as introduced into the reaction tube had reacted.

EXAMPLES 2-3 AND 2-4

Catalytic gas phase oxidation reactions of acrolein were carried out in the same way as of Example 2-1 except that: the catalysts were packed in such a manner that the combination, the order, and the layer length would be those as listed in Table 2, and the composition of the mixed gas was changed in the following composition. The reaction was continuously carried out for 4,000 hours, and the results as obtained when 100 hours and 4,000 hours each passed from the beginning of the reaction are listed in Table 5.

Acrolein: 5.0 volume %
Air: 30.0 volume %
Water vapor: 30.0 volume %
Nitrogen: 35.0 volume %

TABLE 4

| Catalyst number | Composition of catalyst | Catalyst size | | | | Molding method | Calcination temperature (° C.) |
| | | Outer diameter D1 (mm) | Diameter of hole D2 (mm) | Thickness T (mm) | Height L (mm) | | |
| --- | --- | --- | --- | --- | --- | --- | --- |
| (2-1) | $Mo_{12}V_{3.3}W_{1.2}Cu_{1.6}$ | 7.0 | 2.0 | 2.5 | 7.0 | tabletting | 380 |
| (2-2) | ↑ | 7.0 | 3.0 | 2.0 | 7.0 | ↑ | 380 |
| (2-3) | $Mo_{12}V_{3.3}W_{1.2}Cu_{1.6}Sb_{0.3}$ | 8.0 | 3.0 | 2.5 | 8.0 | supporting | 400 |
| (2-4) | ↑ | 7.0 | 2.0 | 2.5 | 7.0 | ↑ | 400 |
| (2-5) | ↑ | 6.0 | 2.0 | 2.0 | 6.0 | ↑ | 400 |

TABLE 5

| | Method for packing catalysts (gas-inlet side → gas-outlet side) | Reaction time (hours) | Reaction temperature (° C.) | Conversion of acrolein (mol %) | Yield of acrylic (mol %) | Selectivity of acrylic acid (mol %) |
| --- | --- | --- | --- | --- | --- | --- |
| Example 2-1 | catalyst (2-2)/catalyst (2-1) = 1000 mm/2000 mm | 100 | 260 | 98.9 | 93.4 | 94.4 |
| | | 4000 | 265 | 99.1 | 93.0 | 93.8 |
| Comparative Example 2-1 | catalyst (2-1) = 3000 mm | 100 | 260 | 99.5 | 89.0 | 89.4 |
| | | 4000 | 265 | 97.9 | 87.5 | 89.4 |
| Comparative Example 2-2 | catalyst (2-1) = 3000 mm | 100 | 260 | 96.3 | 92.0 | 95.5 |
| | | 4000 | 265 | 96.1 | 91.3 | 95.0 |
| Example 2-2 | catalyst (2-2)/catalyst (2-1) = 1000 mm/2000 mm | 100 | 260 | 99.0 | 93.0 | 93.9 |
| | | 4000 | 265 | 98.7 | 92.5 | 93.7 |
| Example 2-3 | catalyst (2-3)/catalyst(2-4)/catalyst (2-5) = 800 mm/800 mm/1400 mm | 100 | 265 | 99.2 | 92.6 | 93.3 |
| | | 4000 | 276 | 99.0 | 92.0 | 92.9 |
| Example 2-4 | catalyst (2-5)/catalyst (2-4)/catalyst (2-3) = 800 mm/800 mm/1400 mm | 100 | 260 | 99.4 | 90.6 | 91.1 |
| | | 4000 | 279 | 99.2 | 89.5 | 90.2 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for an unsaturated aldehyde and/or an unsaturated carboxylic acid, which comprises the step of carrying out catalytic gas phase oxidation of at least one compound selected from the group consisting of propylene, isobutylene, t-butyl alcohol, and methyl t-butyl ether as a raw material with molecular oxygen or a molecular-oxygen-containing gas by using a fixed-bed multitubular reactor which is packed with catalysts, thereby producing the unsaturated aldehyde and/or the unsaturated carboxylic acid which correspond to the raw material;

wherein: the catalysts include, as catalytic components, an oxide and/or a complex oxide including molybdenum, bismuth, and iron as essential components, and are particulate catalysts that have a hole;

a catalyst-packed layer of each reaction tube of the fixedbed multitubular reactor is divided into at least two reaction zones in a tubular axial direction, wherein the packing of the catalysts is such that the diameters of the holes of the catalysts differ between at least two of the reaction zones; and wherein the catalyst-packed layer of each reaction tube is provided with three reaction zones consisting of a first reaction zone, a second reaction zone and a third reaction zone in order from the gas-inlet side, wherein: the diameter of the hole of the catalyst in the second reaction zone is smaller than that in the first reaction zone; and the outer diameter of the catalyst in the third reaction zone is smaller than that in the second reaction zone.

2. A production process according to claim 1, wherein the packing of the catalysts different as to the diameter of the hole is such that the diameter of the hole decreases from the gas-inlet-side reaction zone of the catalyst-packed layer toward the gas-outlet-side reaction zone thereof in each reaction tube.

3. A production process according to claim 1, wherein the catalysts are cylindrical catalysts.

* * * * *